(12) United States Patent
Kirk

(10) Patent No.: US 6,683,054 B1
(45) Date of Patent: Jan. 27, 2004

(54) USE OF MELAGATRAN

(75) Inventor: Ian Kirk, Leicester (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/508,762

(22) PCT Filed: Jan. 13, 2000

(86) PCT No.: PCT/SE00/00051

§ 371 (c)(1),
(2), (4) Date: Mar. 16, 2000

(87) PCT Pub. No.: WO00/41716

PCT Pub. Date: Jul. 20, 2000

(30) Foreign Application Priority Data

Jan. 13, 1999 (SE) .............................. 9900070

(51) Int. Cl.$^7$ .......................... C07K 5/00; A61K 38/55
(52) U.S. Cl. ............................ 514/18; 514/210; 514/2; 435/214; 530/300; 530/331
(58) Field of Search ............... 514/18, 2, 210; 435/214; 530/300, 331

(56) References Cited

U.S. PATENT DOCUMENTS 6,232,315 B1  5/2001  Shafer et al. .......... 514/255.05

FOREIGN PATENT DOCUMENTS

| WO | 94/29336 | 12/1994 | | |
|---|---|---|---|---|
| WO | 97/23499 | 7/1997 | | |
| WO | 97/25994 | 7/1997 | | |
| WO | 97/39770 | 10/1997 | | |
| WO | WO97/39770 | * 10/1997 | .......... | A61K/38/55 |
| WO | WO98/16252 | * 4/1998 | .......... | A61K/47/34 |
| WO | 00/14110 | 3/2000 | | |
| WO | 00/18352 | 4/2000 | | |
| WO | 00/64470 | 11/2000 | | |

OTHER PUBLICATIONS

Cirino et al, "Thrombin Functions as an Inflammatory Mediator . . . ," J. Exp. Med., vol. 183, pp. 821–827 (1996).

Goldsack et al, "Molecules in focus Thrombin," The Int'l Journal of Biochemistry & Cell Biology, vol. 30, pp. 641–646 ;(1998).

Morris et al, "Thrombin in inflammation and healing . . . " Annals of the Rheumatic Diseases, vol. 53, p. 72 (1994).

Eriksson, et al.; "Melagatran, a Low Molecular Weight Thrombin Inhibitor, Counteracts Endotoxin–induced Haemadynamic and Renal Dysfunctions in the Pig"; Thromb Haemost 1998; 80: pp. 1022–1026.

* cited by examiner

Primary Examiner—Christopher S. F. Low
Assistant Examiner—Chih-Min Kam
(74) Attorney, Agent, or Firm—Nixon & Vanderhye

(57) ABSTRACT

According to the invention there is provided the use of melagatran, or a pharmaceutically acceptable derivative or prodrug thereof, in the manufacture of a medicament for the treatment of inflammation.

22 Claims, No Drawings

USE OF MELAGATRAN

This application is a 371 of PCT/SE00/00051, filed Jan. 13, 2000.

FIELD OF THE INVENTION

This invention relates to a new use of the low molecular weight thrombin inhibitor, melagatran.

INTRODUCTION

Inflammation is a localised protective response elicited by injury or destruction of tissues, which serves to destroy, dilute or sequester both the injurious agent and the injured tissue.

Inflammation may result from physical trauma, infection, some chronic diseases (e.g. psoriasis and autoimmune diseases, such as rheumatoid arthritis) and/or chemical and/or physiological reactions to external stimuli (e.g. as part of an allergic response). A complex series of events may be involved, in which inflammatory mediators increase blood flow and dilation of local blood vessels, resulting in redness and heat, the exudation of fluids, often resulting in localised swelling, leukocytic migration into the inflamed area, and pain.

Current local and systemic treatments of inflammation, which treatments are employed typically when inflammation is an inappropriate response (e.g. in the treatment of autoimmune diseases), or is uncomfortable and/or inconvenient, include the administration of inter alia non-steroidal anti-inflammatory agents (NSAIDs), opioid analgesics and corticosteroids.

PRIOR ART

International patent application WO 94/29336 discloses a group of compounds that are useful as inhibitors of serine proteases, such as thrombin and/or kininogenases, such as kallikrein. The thrombin-inhibiting compounds are thus indicated as anticoagulants, and the kininogenase-inhibiting compounds as antiinflammatory agents.

One of the thrombin inhibiting compounds that is specifically disclosed in WO 94/29336 is HOOC—CH$_2$—(R)Cgl-Aze-Pab-H, which is also known as melagatran (see Example 1 of WO 94/29336, and the list of abbreviations in this document). The use of melagatran in the inhibition of kininogenases, and therefore in the treatment of inflammation, is neither mentioned nor suggested.

DISCLOSURE OF THE INVENTION

We have now found, surprisingly, that melagatran elicits a notable antiinflammatory effect, for example as described below, and may thus be used to treat inflammation in preferably mammalian, and especially human, patients.

According to a first aspect of the invention there is provided the use of melagatran, or a pharmaceutically acceptable derivative or prodrug thereof, in the manufacture of a medicament for the treatment of inflammation.

The term "inflammation" will be understood by those skilled in the art to include any condition characterised by a localised protective response elicited by injury or destruction of tissues resulting from any of the causes mentioned hereinbefore, and which is manifest by heat, swelling, pain, redness, dilation of blood vessels and/or increased blood flow, invasion of the affected area by white blood cells, loss of function and/or any other symptoms known to be associated with the inflammatory condition. The term will thus be understood to include inter alia acute, chronic, ulcerative, specific, allergic and necrotic inflammation, as well as all other forms of inflammation known to those skilled in the art.

Melagatran, and derivatives and prodrugs thereof, may thus be used in the direct treatment of inflammation resulting from injury, from viral or bacterial infection, or from a disease characterised by inflammation as one of its symptoms. Such diseases include autoimmune diseases, such as rheumatoid arthritis, psoriasis, allergy, asthma, rhinitis, pancreatitis, uticaria and inflammatory bowel syndrome.

However, melagatran, and derivatives and prodrugs thereof, are preferably used in the treatment of inflammation in patients with, or at risk of, a disease in which inhibition of thrombin is desired or required (see, for example, those listed in international patent application WO 97/23499), such as a thrombotic disease. Although the treatment may be of patients whose inflammatory and thrombotic diseases are unrelated, we prefer that the treatment is of a patient with a thrombotic disease in which inflammation plays a part in triggering coagulation. For example, inflammation may arise in blood vessel walls due to the presence and/or the action of microbes and/or the agents released thereby, physical damage, atheroscelorotic lesions and other inflammation-inducing agents. It is preferred that melagatran, and derivatives and prodrugs thereof, are used in the treatment of inflammation in patients having, or at risk of having, a thrombus.

For the avoidance of doubt, as used herein, the term "treatment" includes the therapeutic and/or prophylactic treatment of inflammation.

"Pharmaceutically acceptable derivatives" includes salts (e.g. pharmaceutically acceptable non-toxic organic or inorganic acid addition salts) and solvates. The term "prodrug" of melagatran includes any compound that, following oral or parenteral administration, is metabolised in vivo to form melagatran (see, for example, international patent application WO 97/23499). Preferred prodrugs are those of the formula R$^1$O$_2$C—CH$_2$—(R)Cgl-Aze-Pab-OH (see the list of abbreviations in WO 97/23499), wherein R$^1$ represents linear or branched C$_{1-6}$ alkyl (e.g. C$_{1-4}$ alkyl, especially methyl, propyl and, particularly, ethyl) and the OH group replaces one of the amidino hydrogens in Pab.

Melagatran, and derivatives and prodrugs thereof, may be administered for systemic delivery to the site of inflammation, or may be administered for delivery directly (locally) to that site, using appropriate means of administration that are known to the skilled person.

Thus, in accordance with the invention, melagatran, and derivatives and prodrugs thereof, may be administered orally, intravenously, subcutaneously, buccally, rectally, dermally, nasally, tracheally, bronchially, topically, by any other parenteral route, or via inhalation, in the form of a pharmaceutical preparation comprising the active ingredient in a pharmaceutically acceptable dosage form. Depending on the disorder, and the patient, to be treated, as well as the route of administration, the compositions may be administered at varying doses.

Preferred modes of delivery are systemic. For melagatran and derivatives thereof, preferred modes of administration are parenteral, more preferably intravenous, and especially subcutaneous. For prodrugs of melagatran, preferred modes of administration are oral.

In the therapeutic treatment of mammals, and especially humans, melagatran and derivatives and prodrugs thereof may be administered alone, but will generally be administered as a pharmaceutical formulation in admixture with a pharmaceutically acceptable adjuvant, diluent or carrier, which may be selected with due regard to the intended route of administration and standard pharmaceutical practice. The preparation of is suitable formulations for use in administering melagatran, derivatives and prodrugs thereof is described in the literature, for example as described in inter alia international patent applications WO 94/29336, WO 96/14084, WO 96/16671, WO 97/23499, WO 97/39770, WO 97/45138, WO 98/16252, WO 99/27912 and WO 99/27913, the disclosures in which documents are hereby incorporated by reference. Otherwise, the preparation of suitable formulations may be achieved non-inventively by the skilled person using routine techniques.

The amounts of melagatran, or derivative or prodrug thereof, in the formulation will depend on the severity of the condition, and on the patient, to be treated, as well as the compound(s) which is/are employed, but may be determined non-inventively by the skilled person.

According to a further aspect of the invention there is provided a pharmaceutical formulation for use in the treatment of inflammation comprising an effective amount of melagatran or a pharmaceutically acceptable derivative or prodrug thereof, in admixture with a pharmaceutically acceptable adjuvant, diluent or carrier.

Melagatran, and derivatives and prodrugs thereof, may also be combined with other therapeutic agents that are useful in the treatment of inflammation (e.g. NSAIDs, corticosteroids and analgesics), and/or other therapeutic agents that are useful in the treatment of a disease characterised by inflammation as one of its symptoms. Melagatran, and derivatives and prodrugs thereof, may also be combined with other therapeutic agents which, when administered, are known to give rise to inflammation as a side-effect. When melagatran, and derivatives and prodrugs thereof, are "combined" with other therapeutic agents in this way, the active ingredients may be administered together in the same formulation, or administered separately (simultaneously or sequentially) in different formulations.

Suitable doses of melagatran, prodrugs and derivatives thereof, in the therapeutic and/or prophylactic treatment of mammalian, especially human, patients are those which give a mean plasma concentration in the range 0.01 to 5 $\mu$mol/L. In any event, the physician, or the skilled person, will be able to determine the actual dosage which will be most suitable for an individual patient, which is likely to vary with the age, weight and response of the particular patient. The above dosages are exemplary of the average case; there can, of course, be individual instances where higher or lower dosage ranges are merited, and such are within the scope of this invention.

The skilled person will also appreciate that melagatran, or a derivative or prodrug thereof, may be administered in an appropriate dose on an "as required" basis (i.e. as needed or desired).

According to a further aspect of the invention there is provided a method of treating inflammation which comprises administering a therapeutically effective amount of melagatran, or a pharmaceutically acceptable derivative or prodrug thereof, to a patient in need of such treatment.

The use and method described herein may have the advantage that, in the treatment of inflammation, melagatran and derivatives and prodrugs thereof may not possess disadvantages of known antiinflammatory agents. The use and method described herein may also have the advantage that melagatran and derivatives and prodrugs thereof may be more efficacious than, be less toxic than, have a broader range of activity than, be more potent than, produce fewer side effects than, be more easily absorbed than, or that they may have other useful pharmacological properties over, compounds known in the prior art for the treatment of inflammation.

The invention is illustrated, but in no way limited, by the following example.

EXAMPLE 1

Groups of five male Charles River CD rats in the weight range 180 to 240 g were used. On their arrival, rats were housed in controlled environment rooms and fed a standard diet for at least one week before use.

Rats were starved overnight before the test, although water was given ad libitum. A mark was made on the ankle joint of each rat, the day before the test, to indicate where the foot volume was to be measured.

Compounds were made up in the appropriate vehicle for dosing via either the subcutaneous (s.c.), intravenous (i.v.) or oral (p.o.) routes. Melagatran was dosed in water (20 $\mu$mol/kg) when given p.o., and in saline, and in cyclodextrin (40%), when given s.c. (0.7 to 2 $\mu$mol/kg). Drugs were administered in a dose volume of 5 mL/kg body weight for p.o. dosing or 1 to 2 mL/kg body weight for s.c. dosing. Control rats received the equivalent volume of vehicle.

A 1% solution of carrageenan in saline was prepared the day prior to the test. The carrageenan was suspended in saline and stirred vigorously on a magnetic stirrer for one hour. It was then stored at 4° C. until required. Thirty minutes after dosing, each rat was injected s.c. in the plantar region of the left hind foot with 0.1 mL of 1% carrageenan.

To reduce both discomfort to the rat and variability in the test, rats were housed on wood chip bedding in solid bottom cages. The rats had access to a solution of 5% glucose throughout the duration of the test.

Foot volumes were measured using a water plethysmograph, the output being displayed using a digital voltmeter and recorded using a Mac-Lab program. The plethysmograph was calibrated using blocks of 2 mL and 4 mL mass before the first, and after the last, measurement at each time point.

Foot volumes were measured before dosing and up to 6 hours after the sub-plantar injection of carrageenan. The increase in foot volume for each rat was calculated using the difference between the individual foot volume at time zero, and at the various time points. The inhibition afforded by a treatment was expressed as a percentage inhibition of the mean absolute increase in foot volume in treated animals compared to control animals. Indomethacin at 10 mg/kg p.o. was always included as an internal standard. If indomethacin gave less than 30% inhibition at 4 h then the test was considered invalid.

A number of standard compounds were tested and the results shown in Table 1.

TABLE 1

| Compound | Dose (route) | % Inhibition after sub-plantar injection | |
|---|---|---|---|
| | | 2 hours after | 4 hours after |
| Indomethacin | 10 mg/kg (p.o.) | 43 | 50 |
| Dexamethasone | 0.3 mg/kg (p.o.) | 51 | 96 |
| Dexamethasone | 0.03 mg/kg (p.o.) | 47 | 74 |
| Ibuprofen | 10 mg/kg (p.o.) | 22 | 26 |

When melagatran was administered orally (20 μmol/kg) in water 30 minutes prior to the sub-plantar injection of carrageenan, it was ineffective in inhibiting paw oedema at up to 6 h post dosing. When given s.c. in cyclodextrin (2 μmol/kg) a 29% inhibition of the oedema was observed at 1 hour (Table 2).

TABLE 2

| Compound | Dose | % Inhibition after | | | |
|---|---|---|---|---|---|
| | | 1 hour | 2 hours | 3 hours | 4 hours |
| Indomethacin | 10 mg/kg (p.o.) | −5 | 50 | 39 | 12 |
| Melagatran | 20 μmol/kg (p.o.) | 14 | 17 | −14 | −2 |
| Melagatran | 2 μmol/kg (s.c.) | 29 | 13 | 3 | 13 |

When melagatran was administered in saline at a dose of 24 μmol/kg s.c., a 39% inhibition of the oedema was observed after 1 h (Table 3).

TABLE 3

| Compound | Dose | % Inhibition after | | | |
|---|---|---|---|---|---|
| | | 1 hour | 2 hours | 3 hours | 4 hours |
| Indomethacin | 10 mg/kg (p.o.) | 15 | 2 | 29 | 18 |
| Melagatran | 2 μmol/kg (s.c.) | 39 | 8 | 2 | −8 |

This finding was investigated further, with melagatran being administered in saline at doses of 0.7, 1.4 and 2 μmol/kg s.c., 30 minutes prior to a sub-plantar injection of carrageenan, with paw oedema being measured at 1, 1.5, 2 and 3 hour time points. The results are shown in Table 4.

TABLE 4

| Compound | Dose | % Inhibition after | | | |
|---|---|---|---|---|---|
| | | 1 hour | 1.5 hours | 2 hours | 3 hours |
| Melagatran | 0.7 μmol/kg (s.c.) | 39 | −1 | 9 | 16 |
| Melagatran | 1.4 μmol/kg (s.c.) | 65 | 40 | 5 | 7 |
| Melagatran | 2.0 μmol/kg (s.c.) | 76 | 41 | 17 | 19 |

Due to the short duration of this experiment, indomethacin controls were not included.

It can be seen clearly that melagatran inhibited paw oedema in both a dose dependent, and time dependent, manner.

What is claimed is:

1. A drug combination comprising melagatran, or a pharmaceutically acceptable derivative of melagatran, said derivative having the inhibitory activity against thrombin or being a prodrug of melagatran, and an anti-inflammatory agent.

2. A drug combination comprising melagatran, or a pharmaceutically acceptable derivative of melagatran, said derivative having the inhibitory activity against thrombin or being a prodrug of melagatran, and an anti-inflammatory agent that is useful in the treatment of a disease characterized by inflammation as one of its symptoms.

3. The combination as claimed in claim 1, wherein the anti-inflammatory agent is a non-steroidal anti-inflammatory drug (NSAID), a corticosteroid or an analgesic.

4. The combination as claimed in claim 1 wherein the melagatran, derivative or prodrug thereof is combined with the anti-inflammatory agent together in the same formulation.

5. The combination as claimed in claim 1 wherein the melagatran, derivative or prodrug thereof, and the anti-inflammatory agent, are administered in different formulations.

6. The combination as claimed in claim 2, wherein the anti-inflammatory agent is an NSAID, a corticosteroid or an analgesic.

7. The combination as claimed in claim 2, wherein the melagatran, derivative or prodrug thereof is combined with the anti-inflammatory agent together in the same formulation.

8. The combination as claimed in claim 2, wherein the melagatran, derivative or prodrug thereof, and the anti-inflammatory agent, are administered in different formulations.

9. The combination as claimed in claim 1, wherein the prodrug is the formula $$R^1O_2C-CH_2-(R)Cgl-Aze-Pab-OH$$

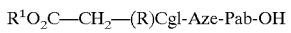

wherein $R^1$ represents linear or branched $C_{1-6}$ alkyl and the OH group replaces one of the amidino hydrogens in Pab.

10. The combination as claimed in claim 9, wherein $R^1$ represents methyl, ethyl, or propyl.

11. The combination as claimed in claim 10, wherein $R^1$ represents ethyl.

12. The combination as claimed in claim 2, wherein the prodrug is the formula $$R^1O_2C-CH_2-(R)Cgl-Aze-Pab-OH$$

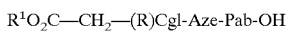

wherein $R^1$ represents linear or branched $C_{1-6}$ alkyl and the OH group replaces one of the amidino hydrogens in Pab.

13. The combination as claimed in claim 12, wherein $R^1$ represents methyl, ethyl, or propyl.

14. The combination as claimed in claim 13, wherein $R^1$ represents ethyl.

15. A method of treatment of inflammation which comprises administering a therapeutically effective amount of a drug combination as claimed in claim 13 to a patient in need of such treatment for a time and under conditions suitable for eliciting an anti-inflammatory effect.

16. The method as claimed in claim 15, wherein the treatment is of inflammation in patients with, or at risk of, a disease in which inhibition of thrombin is desired or required.

17. The method as claimed in claim 16, wherein the disease is one in which inflammation plays a part in triggering coagulation.

18. The method as claimed in claim 16, wherein the patient has, or is at risk of, a thrombus.

19. A method of treatment of inflammation which comprises administering a therapeutically effective amount of a drug combination as claimed in claim 2 to a patient in need of such treatment for a time and under conditions suitable for eliciting an anti-inflammatory effect.

20. The method as claimed in claim 19, wherein the treatment is of inflammation in patients with, or at risk of, a disease in which inhibition of thrombin is desired or required.

21. The method as claimed in claim 20, wherein the disease is one in which inflammation plays a part in triggering coagulation.

22. The method as claimed in claim 20, wherein the patient has, or is at risk of, a thrombus.

* * * * *